(12) United States Patent
Badie et al.

(10) Patent No.: US 11,745,018 B2
(45) Date of Patent: *Sep. 5, 2023

(54) METHOD AND SYSTEM FOR DYNAMIC DEVICE-BASED DELAY ADJUSTMENT

(71) Applicant: Pacesetter, Inc, Sylmar, CA (US)

(72) Inventors: Nima Badie, Berkeley, CA (US); Carin Folman, Bedford, MA (US); Jennifer Rhude, Carbondale, IL (US); Aditya Goil, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/590,462

(22) Filed: Feb. 1, 2022

(65) Prior Publication Data

US 2022/0233864 A1    Jul. 28, 2022

Related U.S. Application Data

(63) Continuation of application No. 16/574,930, filed on Sep. 18, 2019, now Pat. No. 11,273,312.

(Continued)

(51) Int. Cl.
*A61N 1/365* (2006.01)
*A61N 1/368* (2006.01)

(52) U.S. Cl.
CPC ....... *A61N 1/3682* (2013.01); *A61N 1/36592* (2013.01)

(58) Field of Classification Search
CPC .............. A61N 1/3627; A61N 1/36592; A61N 1/3682; A61N 1/375; A61B 5/0816;

(Continued)

(56) References Cited

U.S. PATENT DOCUMENTS 7,643,878 B1    1/2010 Muller
11,273,312 B2 *   3/2022 Badie .................. A61B 5/363

(Continued)

OTHER PUBLICATIONS

International Search Report and Written Opinion for corresponding Application No. PCT/US20199/051949 dated Dec. 11, 2019 (16 pages).

(Continued)

*Primary Examiner* — Jon Eric C Morales

(74) *Attorney, Agent, or Firm* — THE SMALL PATENT LAW GROUP LLC; Dean D. Small

(57) ABSTRACT

A method and device for dynamic device based AV delay adjustment is provided. The method comprises electrodes that are configured to be located proximate to an atrial (A) site and a right ventricular (RV) site. The method utilizes one or more processors for detecting an atrial paced (Ap) event or atrial sensed (As) event, and measures an AV interval corresponding to an interval between the Ap event or the As event and a sensed ventricular (Vs) event. The AV interval is associated with a current heart rate (HR). The method automatically dynamically adjusts a first AV delay based directly on the measured AV interval, identifies a scale factor associated with the current HR, calculates a second AV delay by scaling the first AV delay based on the scale factor and manages a pacing therapy, utilized by the IMD, based on the first and second AV delays.

19 Claims, 5 Drawing Sheets

Related U.S. Application Data

(60) Provisional application No. 62/734,817, filed on Sep. 21, 2018.

(58) Field of Classification Search
CPC ......... A61B 5/287; A61B 5/349; A61B 5/363; A61B 5/686; A61B 5/6869
See application file for complete search history.

(56) References Cited

U.S. PATENT DOCUMENTS

| | | |
|---|---|---|
| 2004/0147966 A1 | 7/2004 | Ding et al. |
| 2008/0140147 A1 | 6/2008 | Husby |
| 2009/0234414 A1 | 9/2009 | Sambelashvili et al. |
| 2009/0281591 A1 | 11/2009 | Shuras et al. |
| 2017/0246460 A1 | 8/2017 | Ghosh |

OTHER PUBLICATIONS

Badie et al. "Programming Cardiac Resynchronization Therapy for Electrical Synchrony: Reaching Beyond Left Bundle Branch Block and Left Ventricular Activation Delay" Journal of American Heart Association; 2018 (13 pages).

International Search Report and Written Opinion for corresponding PCT Application No. PCT/US2019/051946 dated Dec. 5, 2019 (16 pages).

* cited by examiner

METHOD AND SYSTEM FOR DYNAMIC DEVICE-BASED DELAY ADJUSTMENT

RELATED APPLICATION

This application is a continuation application of and claims priority to U.S. application Ser. No. 16/574,930 filed 18 Sep. 2019, which claims priority to U.S. Provisional Application No. 62/734,817, filed 21 Sep. 2018, the entire disclosure of each are incorporated by reference herein in their entirety.

FIELD OF THE INVENTION

Embodiments herein generally relate to implantable medical devices, and more particularly to adjusting atrioventricular delays in connection with intrinsic and paced atrial activity.

BACKGROUND OF THE INVENTION

Advances in implantable medical devices (IMD) and left ventricular (LV) lead design has improved electrical stimulation, delays, and pacing, resulting in a better patient outcome. Loss of atrioventricular (AV) electrical and mechanical synchrony can result in inadequate ventricular depolarization, leading to suboptimal therapy. Optimal AV delay (AVD) can improve electrical synchrony by fusing an intrinsic conduction wavefront and device pacing to produce an enhanced depolarization of the ventricles and increased cardiac output.

Cardiac resynchronization therapy (CRT) has been shown to improve hemodynamics in heart failure (HF) patients, particularly when the AVD has been individualized for each patient. AVD programming for each patient is commonly performed in-clinic at implant, when an AVD is selected for each patient based on echocardiographic, ECG, or blood pressure metrics. This one-time, static AVD selection does not account for short-term changes (hourly; e.g., exercise, sleep) or long-term changes (monthly; e.g., disease progression) in a patient's electromechanical conduction after the patient leaves the clinic.

At least one approach has been proposed that adjusts the AVD over time. In this conventional approach, an AV interval (AVI) is measured and the AVD is set to equal the AV interval reduced by a fixed amount that the clinician programs. Periodically, the conventional approach prolongs the AVD in order to re-measure the intrinsic AV interval. The approach programs two distinct AV delays in parallel: the AVD after a sensed atrial event (AVDs) and the AVD after a paced atrial event (AVDp).

However, the conventional approach experiences certain limitations in connection with two use cases relating to AVDs and AVDp. The first use case occurs when the intrinsic AV interval is measured during atrial sensing (e.g., As-Vs event: intrinsic atrial beat is sensed by the RA lead [As] and then an intrinsic ventricular beat is sensed by the RV lead [Vs]). The As-related intrinsic AV interval is used to calculate the new AVDs value that is used to deliver ventricular pacing (Vp) after each subsequent As event. However, a new AVDp value is also programmed to handle any potential atrial paced events. In the current approach, the AVDp is set to equal the AVDs plus a fixed time period set by the clinician. In other words, the conventional approach indirectly calculates the new AVDp by extending the AVDs by the difference between the longer default paced and sensed AVD values programmed in-clinic.

The second use case occurs when an intrinsic AV interval is measured during atrial pacing (e.g., Ap-Vs event: paced atrial beat is delivered by the RA lead [Ap] and then an intrinsic ventricular beat is sensed by the RV lead [Vs]). The Ap-related intrinsic AV interval is used to calculate the new AVDp value that is used to deliver Vp after each subsequent Ap event. Like the scenario described above, a new AVDs value is also programmed to handle any potential atrial sensed events. In the current approach, the AVDs is set equal to the AVDp minus a fixed time period set by the clinician.

Typically, clinicians set the AVDp-default to be greater than the AVDs-default to account for the difference between the following intervals: (i) conduction time from an atrial paced beat to the ventricular lead (Ap-Vs) and (ii) time from an intrinsic sinoatrial nodal beat being sensed by the atrial lead to the time when that same beat is sensed by the ventricular lead (As-Vs). However, the difference between the programmed default AVDs-default and AVDp-default values is typically not based on patient-specific conduction measurements. The nature of the original atrial event (i.e., As or Ap) matters when attempting to provide synchronous therapy. When the conventional approach reprograms both the AVDs and AVDp, the device may switch from atrial sensing to atrial pacing (or vice versa) during an extended series of beats (e.g., 32 beats or 256 beats). During the extended series of beats, in which the device delivers atrial pacing, the device also uses the indirectly calculated AVDp value to determine when to deliver ventricular pacing. The AVDp is not directly calculated from a measured Ap-Vs interval, and thus a potential exists that the device is not timing the ventricular paced event in a desired manner. Given that the AVDp is not patient-specific, the indirectly calculated AVDp may not provide proper AV synchrony. Similarly, when the conventional approach measures the Ap-Vs interval in connection with an atrial paced event, the conventional approach programs the AVDs in directly. Thus a potential exists that the device is not timing the ventricular paced event in a desired manner. Given that the AVDs is not patient-specific, the indirectly calculated AVDs may not provide proper AV synchrony.

A need remains for methods and systems that provide dynamic AV timing adjustment that adapts to each patient's continually changing cardiovascular status.

SUMMARY

In accordance with embodiments herein, a method for dynamic device based AV delay adjustment is provided. The method comprises electrodes that are configured to be located proximate to an atrial (A) site and a right ventricular (RV) site. The method utilizes one or more processors for detecting an atrial paced (Ap) event or atrial sensed (As) event, and measures an AV interval corresponding to an interval between the Ap event or the As event and a sensed ventricular (Vs) event. The AV interval is associated with a current heart rate (HR). The method automatically dynamically adjusts a first AV delay based directly on the measured AV interval, identifies a scale factor associated with the current HR, calculates a second AV delay by scaling the first AV delay based on the scale factor and manages a pacing therapy, utilized by the IMD, based on the first and second AV delays.

Optionally, the AV interval measured may represent a measured As-Vs interval and the first AV delay may represent a sensed AV delay (AVDs) that may be calculated by subtracting an offset from the measured As-Vs interval. The second AV delay may represent a paced AV delay (AVDp)

that may be calculated by multiplying or dividing the AVDs by the scale factor. The scale factor may represent a ratio between a base As-Vs interval and a base Ap-Vs interval.

The AV interval measured may represent a measured Ap-Vs interval and the first AV delay may represent a paced AV delay (AVDp) that may be calculated by subtracting an offset from the measured Ap-Vs interval. The second AV delay may represent a sensed AV delay (AVDs) that may be calculated by multiplying or dividing the AVDp by the scale factor.

Optionally, the method may further comprise measuring a base As-Vs interval and a base Ap-Vs interval during a common base HR range. The method may calculate the scale factor as a ration between the base As-Vs interval and Ap-Vs interval and may store the scale factor in connection with the base HR range. The identifying operation may further comprise identifying the scale factor based on a correlation between the current HR and the base HR range. The method may further comprise repeating the measuring, calculating and storing operations in connection with different base HR ranges to obtain a plurality of the base As-Vs intervals and the base Ap-Vs intervals associated with the different base HR ranges. The identifying operation may comprise identifying a select base HR range from the base HR ranges that may correspond to the current HR and may utilize the scale factor associated with the select base HR range to calculate the second AV delay.

Optionally, during a search window, the method may extend the first and second AV delays to correspond to a default search AV delay ($AVD_{search}$). The method may sense cardiac activity for a predetermined number of cardiac beats during the search window, may identify whether the cardiac activity is indicative of a conduction block condition or non-conduction block condition and may repeat the determining, calculating and adjusting operations only when the non-conduction block condition is identified. The identifying operation may comprise identifying the cardiac activity to be indicative of a conduction block condition when fewer than a select number of cardiac beats exhibit sensed ventricular events during the default search AV delay $AVD_{search}$. The scale factor may be between a base As-Vs interval and a base Ap-Vs interval.

In accordance with embodiments herein, an implantable medical device (IMD) is provided. The device comprises electrodes that are configured to be located proximate to an atrial (A) site and a right ventricular (RV) site. Memory stores program instructions. One or more processors are configured to implement the program instructions to detect an atrial paced (Ap) event or atrial sensed (As) event, and measure an AV interval corresponding to an interval between the Ap event or the As event and a sensed ventricular (Vs) event. The AV interval is associated with a current heart rate (HR). The method automatically dynamically adjust a first AV delay based directly on the measured AV interval and identifies a scale factor between a base As-Vs interval and a base Ap-Vs interval associated with the current HR. The method calculates a second AV delay by scaling the first AV delay based on the scale factor and manages a pacing therapy, utilized by the IMD, based on the first and second AV delays.

Optionally, the AV interval measured may represent a measured As-Vs interval and the first AV delay may represent a sensed AV delay (AVDs) that may be calculated by subtracting an offset from the measured As-Vs interval. The second AV delay may represent a paced AV delay (AVDp) that may be calculated by multiplying or dividing the AVDs by the scale factor. The AV interval measured may represent a measured Ap-Vs interval and the first AV delay may represent a paced AV delay (AVDp) that may be calculated by subtracting an offset from the measured Ap-Vs interval. The second AV delay may represent a sensed AV delay (AVDs) that may be calculated by multiplying or dividing the AVDp by the scale factor.

Optionally, the one or more processors may be further configured to measure the base As-Vs interval and the base Ap-Vs interval during a common base HR range. The device may store the scale factor in connection with the base HR range. The identify operation may further comprise identifying the scale factor based on the current HR with the base HR range. The one or more processors may be further configured to repeat the measure and may store operations in connection with different base HR ranges to obtain a plurality of the base As-Vs intervals and the base Ap-Vs intervals associated with the different base HR ranges. The identify operation may comprise identifying a select base HR range from the base HR ranges that may corresponds to the current HR and may utilizes the scale factor associated with the select base HR range to calculate the second AV delay.

Optionally, during a search window, the one or more processors may extend the first and second AV delays to correspond to a default search AV delay ($AVD_{search}$). The processors may sense cardiac activity for a predetermined number of cardiac beats during the search window, may identify whether the cardiac activity is indicative of a conduction block condition or non-conduction block condition and may repeat the determine, calculate and adjust operations only when the non-conduction block condition is identified.

In accordance with embodiments herein, a method for dynamic device based A-HIS delay adjustment is provided. The method provides electrodes that are configured to be located proximate to an atrial (A) site and a HIS bundle (HIS) site. The method utilizes utilizing one or more processors for detecting an atrial paced (Ap) event or atrial sensed (As) event and measuring an A-HIS interval corresponding to an interval between the Ap event or the As event and a sensed HIS bundle event. The AV interval is associated with a current heart rate (HR). The method automatically dynamically adjusting a first A-HIS delay based directly on the measured A-HIS interval and identifies a scale factor associated with the current HR. The method calculates a second A-HIS delay by scaling the first A-HIS delay based on the scale factor and manages a pacing therapy, utilized by the IMD, based on the first and second A-HIS delays.

Optionally, the A-HIS interval measured may represent a measured As-HIS interval and the first A-HIS delay may represent a sensed A-HIS delay that may be calculated by subtracting an offset from the measured As-HIS interval. The second A-HIS delay may represent a paced A-HIS delay that may be calculated by multiplying or dividing the sensed A-HIS delay by the scale factor. The scale factor may representing a ratio between a base As-HIS interval and a base Ap-HIS interval.

DETAILED DESCRIPTION

Figure 1:
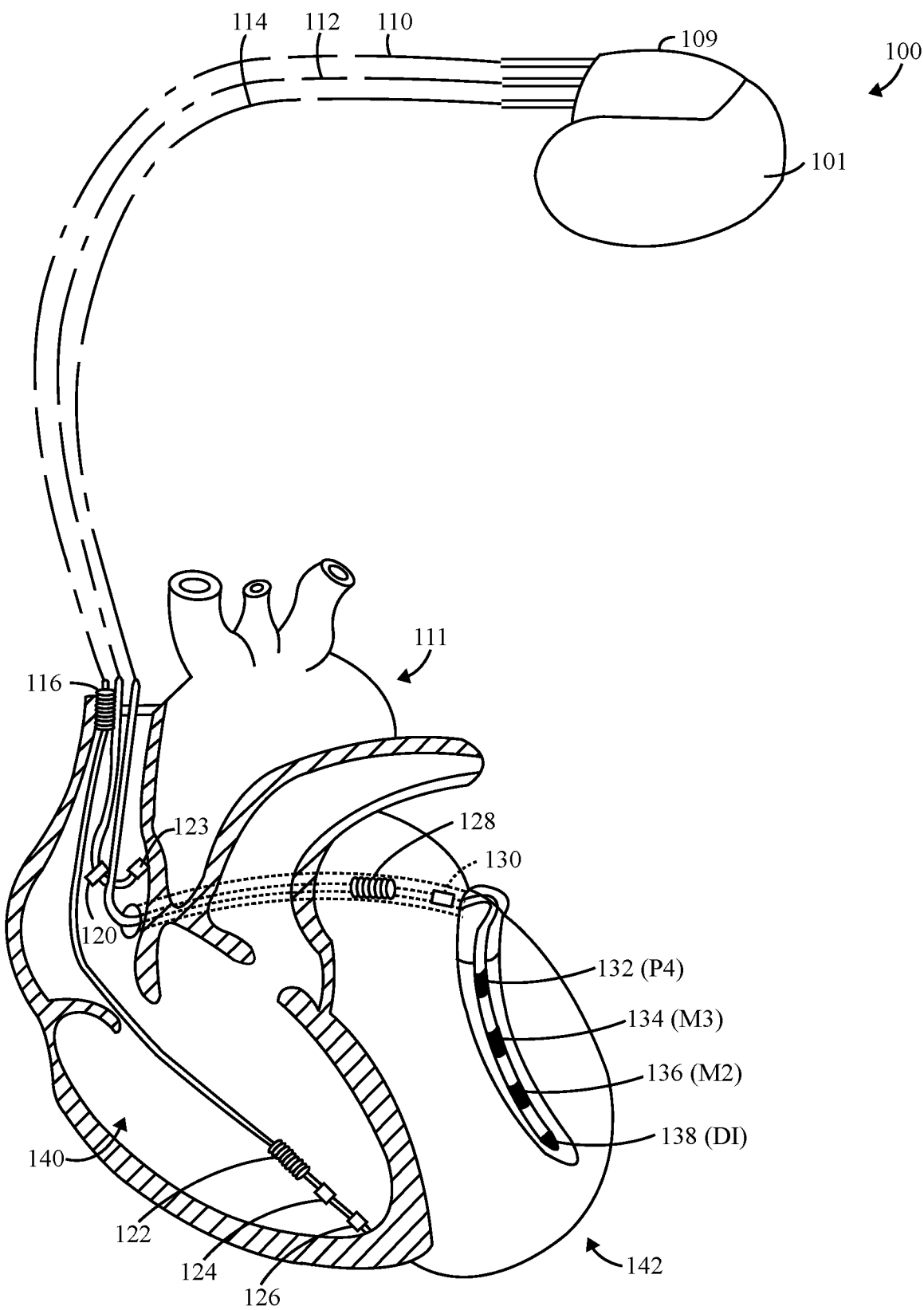
FIG. 1 illustrates an implantable medical device (IMD) intended for subcutaneous implantation at a site near the heart in accordance with embodiments herein.

The term "As-Vs interval", as used herein, refers to a measured intrinsic conduction time from a sensed atrial (As) event to a sensed ventricular (Vs) event. The sensed ventricular event may be a right ventricular event or a left ventricular event. The term "Ap-Vs interval", as used herein, refers to a measured intrinsic conduction time from a paced atrial (Ap) event to a sensed ventricular (Vs) event. The sensed ventricular event may be a right ventricular event or a left ventricular event.

The term "As-RVs interval", as used herein, refers to a measured intrinsic conduction time from a sensed atrial (As) event to a sensed right ventricular (RVs) event. The term "Ap-RVs interval", as used herein, refers to a measured intrinsic conduction time from a paced atrial (Ap) event to a sensed right ventricular (RVs) event.

The term "As-LVs interval", as used herein, refers to a measured intrinsic conduction time from a sensed atrial (As) event to a sensed left ventricular (LVs) event. The term "Ap-LVs interval", as used herein, refers to a measured intrinsic conduction time from a paced atrial (Ap) event to a sensed left ventricular (LVs) event.

The terms "atrioventricular delay" and "AVD" refer to a programmed time delay to be used by the implantable medical device in connection with delivering therapy.

The term "AVDs" refers to an AVD in connection with delivering therapy at a ventricular site following a sensed atrial event, when an intrinsic ventricular event does not occur before AVDs expires.

The term "AVDp" refers to an AVD in connection with delivering therapy at a ventricular site following a paced atrial event, when an intrinsic ventricular event does not occur before AVDp expires.

The term "A-LVDp" refers to an AVD in connection with delivering therapy at a left ventricular site following a paced atrial event, when an intrinsic left ventricular event does not occur before A-LVDp expires.

The term "A-LVDs" is used to refer to an AVD in connection with delivering therapy at a left ventricular site following an intrinsic sensed atrial event, when an intrinsic left ventricular event does not occur before A-LVDs expires.

The term "LV only pacing" refers to a mode of operation for an implanted medical device in which the LV is paced but the RV is not paced.

In accordance with embodiments herein, methods and systems are described for dynamic adjustment of AVD while accounting for a dependence changes in a nature of atrial events between atrial paced events and atrial sensed events. Embodiments herein dynamic adjustment of AVDs and AVDp while addressing differences between As-Vs and Ap-Vs intervals in a patient-specific manner. The As-Vs and Ap-Vs intervals are directly measured at similar heart rates, and a paced/sensed (P/S) scale factor is calculated as a ratio between measured base AV intervals originating with sensed and paced atrial events (R=base Ap-Vs/base As-Vs). During operation, when the As-Vs interval is measured in a search window and used to define the AVDs, a corresponding scaled AVDp value is calculated based on the AVDs and scale factor, such as AVDp=AVDs×R. Alternatively, when the Ap-Vs interval is measured during a search window and used to define the AVDp, a corresponding scaled AVDs value is calculated based on the AVDp and scale factor, such as AVDs=AVDp/R. Using the scale factor to convert between AVDp and AVDs values, embodiments herein account for (factor in) the patient-specific difference in As-Vs and Ap-Vs intervals which depend on relative locations of the atrial lead, sinoatrial node and atrioventricular node, as well as the respective conduction velocities. Also, using the scale factor to convert between AVDp and AVDs values, embodiments herein, dividing out any dependence of the As-Vs and Ap-Vs intervals on heart rate (HR).

Embodiments herein may be implemented in connection with IMDs that provide right side pacing (e.g., an RA lead and a RV lead) and/or in connection with IMDs that provide biventricular pacing (e.g., an RA lead, an RV lead and an LV lead such as a quadripolar LV lead).

FIG. 1 illustrates an implantable medical device (IMD) 100 intended for subcutaneous implantation at a site near the heart 111, in accordance with embodiments herein. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like. The IMD 100 may include a housing 101 to hold the electronic/computing components. The housing 101 (which is often referred to as the "can," "case," "encasing," or "case electrode") may be programmably selected to act as the return electrode for certain stimulus modes. The housing 101 further includes a connector 109 with a plurality of terminals 200-210 (shown in FIG. 2).

The IMD 100 is shown in electrical connection with a heart 111 by way of a left atrial (LA) lead 120 having a right lead 112 and a left atrial (LA) ring electrode 128. The IMD 100 is also in electrical connection with the heart 111 by way of a right ventricular (RV) lead 110 having, in this embodiment, a left ventricle (LV) electrode 132 (e.g., P4), an LV electrode 134 (e.g., M3), an LV electrode 136 (e.g., M2), and an LV electrode 138 (e.g., D1). The RV lead 110 is transvenously inserted into the heart 111 to place the RV coil 122 in the RV apex, and the SVC coil electrode 116. Accordingly, the RV lead 110 is capable of receiving cardiac signals and delivering stimulation in the form of pacing and shock therapy to the right ventricle 140 (also referred to as the RV chamber). The IMD 100 includes RV tip electrode 126, and a right atrium (RA) electrode 123. The RV lead 110 includes an RV tip electrode 126, an RV ring electrode 124, an RV coil electrode 122, and an SVC coil electrode 116.

The IMD 100 includes a left ventricle 142 (e.g., left chamber) pacing therapy, and is coupled to a multi-pole LV lead 114 designed for placement in various locations such as a "CS region" (e.g., venous vasculature of the left ventricle, including any portion of the coronary sinus (CS), great cardiac vein, left marginal vein, left posterior ventricular vein, middle cardiac vein, and/or small cardiac vein or any other cardiac vein accessible by the coronary sinus), the epicardial space, and/or the like.

In an embodiment, the LV lead 114 is designed to receive atrial and ventricular cardiac signals and to deliver left ventricular pacing therapy using a set of multiple LV electrodes 132, 134, 136, 138. The LV lead 114 also may deliver left atrial pacing therapy using at least an LA ring electrode 128 and shocking therapy using at least the LA ring electrode 128. In alternate embodiments, the LV lead 114 includes the LV electrodes 138, 136, 134, and 132, but does not include the LA electrode 130. The LV lead 114 may be, for example, the Quartet™ LV pacing lead developed by St. Jude Medical Inc. (headquartered in St. Paul, Minn.), which includes four pacing electrodes on the LV lead. Although three leads 110, 112, and 114 are shown in FIG. 1, fewer or additional leads with various configurations of pacing, sensing, and/or shocking electrodes may optionally be used. For example, the LV lead 114 may have more or less than four LV electrodes 132-138.

The LV electrode 132 (also referred to as P4) is shown as being the most "distal" LV electrode with reference to how far the electrode is from the right ventricle 140. The LV electrode 138 (also referred to as D1) is shown as being the most "proximal" LV electrode 132-138 to the left ventricle 142. The LV electrodes 136 and 134 are shown as being "middle" LV electrodes (also referred to as M3 and M2), between the distal and proximal LV electrodes 138 and 132, respectively. Accordingly, so as to more aptly describe their relative locations, the LV electrodes 138, 136, 134, and 132 may be referred to respectively as electrodes D1, M2, M3, and P4 (where "D" stands for "distal", "M" stands for "middle", and "P" stands from "proximal", and the s are arranged from most distal to most proximal, as shown in FIG. 1). Optionally, more or fewer LV electrodes may be provided on the lead 114 than the four LV electrodes D1, M2, M3, and P4.

The LV electrodes 132-138 are configured such that each electrode may be utilized to deliver pacing pulses and/or sense pacing pulses (e.g., monitor the response of the LV tissue to a pacing pulse). In a pacing vector or a sensing vector, each LV electrode 132-138 may be controlled to function as a cathode (negative electrode). Pacing pulses may be directionally provided between electrodes to define a pacing vector. In a pacing vector, a generated pulse is applied to the surrounding myocardial tissue through the cathode. The electrodes that define the pacing vectors may be electrodes in the heart 111 or located externally to the heart 111 (e.g., on a housing/case device 101). For example, the housing/case 101 may be referred to as the housing 101 and function as an anode in unipolar pacing and/or sensing vectors. The RV coil 122 may also function as an anode in unipolar pacing and/or sensing vectors. The LV electrodes 132-138 may be used to provide various different vectors. Some of the vectors are intraventricular LV vectors (e.g., vectors between two of the LV electrodes 132-138), while other vectors are interventricular vectors (e.g., vectors between an LV electrode 132-138 and the RV coil 122 or another electrode remote from the left ventricle 142). Various exemplary bipolar sensing vectors with LV cathodes that may be used for sensing using the LV electrodes D1, M2, M3, and P4 and the RV coil 122. Various other types of leads and the IMD 100 may be used with various other types of electrodes and combinations of electrodes. Utilizing an RV coil electrode as an anode is merely one example. Various other electrodes may be configured as the anode electrode.

Additionally or alternatively, a lead may be implanted with one or more electrodes that are located proximate to the HIS bundle. Optionally, one or more of the leads illustrated in FIG. 1 may be provided with one or more additional electrodes that are located proximate to the HIS bundle. The electrodes located proximate to the HIS bundle may be configured to sense electrical activation at the HIS bundle and/or deliver pacing pulses to the HIS bundle.

Figure 2:
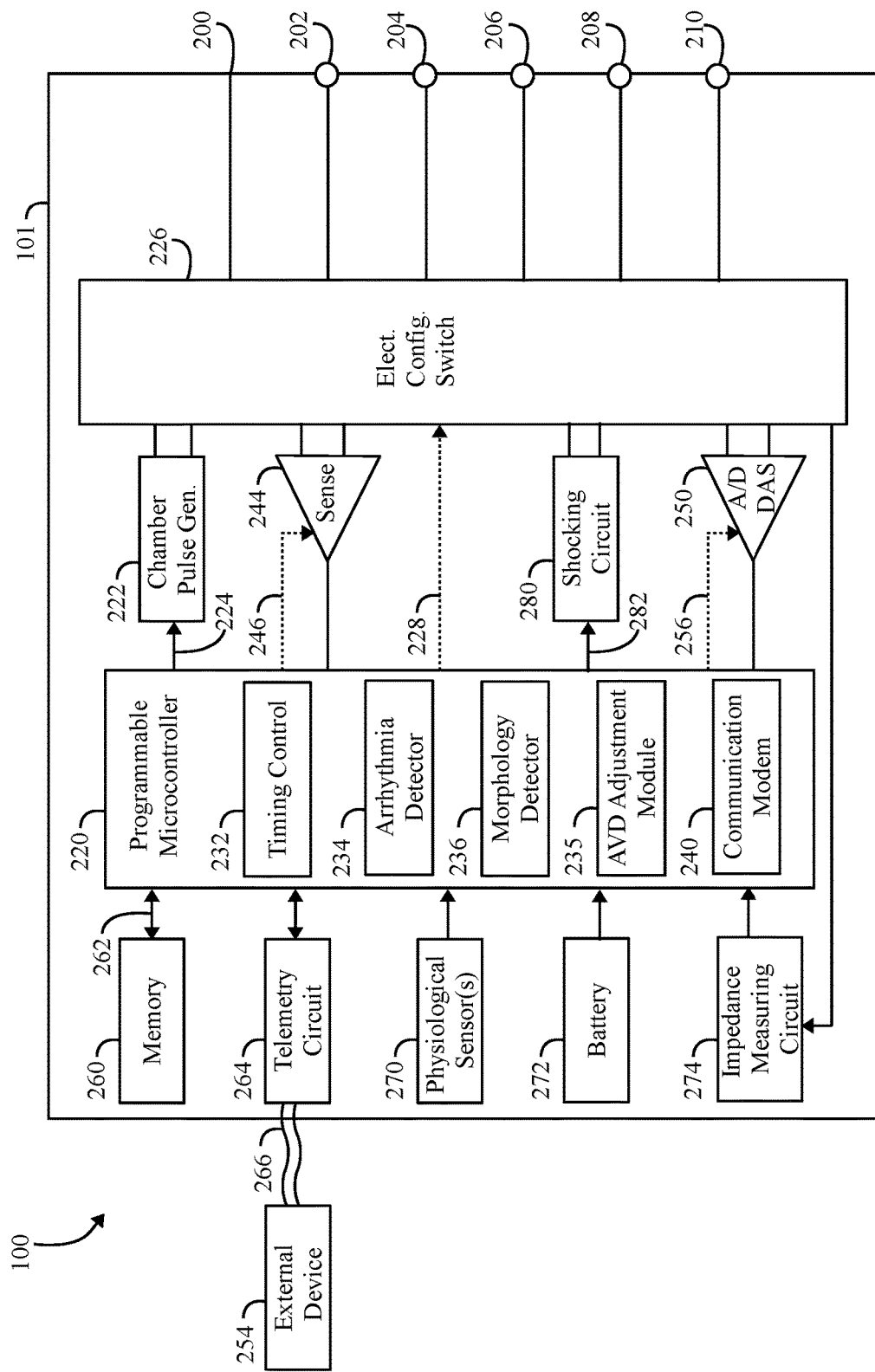
FIG. 2 illustrates a schematic view of the IMD in accordance with embodiments herein.

FIG. 2 illustrates a schematic view of the IMD 100. The IMD 100 may be a dual-chamber stimulation device, capable of treating both fast and slow arrhythmias with stimulation therapy, including cardioversion, pacing stimulation, an implantable cardioverter defibrillator, suspend tachycardia detection, tachyarrhythmia therapy, and/or the like.

The IMD 100 has a housing 101 to hold the electronic/computing components. The housing 101 (which is often referred to as the "can," "case," "encasing," or new to me makes "case electrode") may be programmably selected to act as the return electrode for certain stimulus modes. The housing 101 further includes a connector (not shown) with a plurality of terminals 200-210. The terminals may be connected to electrodes that are located in various locations within and around the heart. For example, the terminals may include: a terminal 200 to be coupled to a first electrode (e.g., a tip electrode) located in a first chamber; a terminal 202 to be coupled to a second electrode located in a second chamber; a terminal 204 to be coupled to an electrode located in the first chamber; a terminal 206 to be coupled to an electrode located in the second chamber; an a terminal 208 to be coupled to an electrode; and a terminal 210 to be coupled to an electrode located in the shocking circuit 280. The type and location of each electrode may vary. For example, the electrodes may include various combinations of a ring, a tip, a coil and shocking electrodes and the like.

The IMD 100 includes a programmable microcontroller 220 that controls various operations of the IMD 100, including cardiac monitoring and stimulation therapy. The microcontroller 220 includes a microprocessor (or equivalent control circuitry), one or more processors, RAM and/or ROM memory, logic and timing circuitry, state machine circuitry, and I/O circuitry. The IMD 100 further includes an atrial and/or ventricular pulse generator 222 that generates stimulation pulses for connecting the desired electrodes to the appropriate I/O circuits, thereby facilitating electrode programmability. The switch 226 is controlled by a control signal 228 from the microcontroller 220.

A pulse generator 222 is illustrated in FIG. 2. Optionally, the IMD 100 may include multiple pulse generators, similar to the pulse generator 222, where each pulse generator is coupled to one or more electrodes and controlled by the microcontroller 220 to deliver select stimulus pulse(s) to the corresponding one or more electrodes. The IMD 100 includes sensing circuits 244 selectively coupled to one or more electrodes that perform sensing operations, through the switch 226 to detect the presence of cardiac activity in the chamber of the heart 111. The output of the sensing circuits 244 is connected to the microcontroller 220 which, in turn, triggers, or inhibits the pulse generator 222 in response to the absence or presence of cardiac activity. The sensing circuits 244 receives a control signal 246 from the microcontroller 220 for purposes of controlling the gain, threshold, polarization charge removal circuitry (not shown), and the timing of any blocking circuitry (not shown) coupled to the inputs of the sensing circuits.

In the example of FIG. 2, the sensing circuit 244 is illustrated. Optionally, the IMD 100 may include multiple sensing circuits 244, similar to the sensing circuit 244, where each sensing circuit is coupled to one or more electrodes and controlled by the microcontroller 220 to sense electrical activity detected at the corresponding one or more electrodes. The sensing circuit 224 may operate in a unipolar sensing configuration or a bipolar sensing configuration.

The IMD 100 further includes an analog-to-digital (ND) data acquisition system (DAS) 250 coupled to one or more electrodes via the switch 226 to sample cardiac signals across any pair of desired electrodes. The DAS 250 is configured to acquire intracardiac electrogram signals, convert the raw analog data into digital data and store the digital data for later processing and/or telemetric transmission to an external device 254 (e.g., a programmer, local transceiver, or a diagnostic system analyzer). The DAS 250 is controlled by a control signal 256 from the microcontroller 220.

The microcontroller 220 includes an arrhythmia detector 234 for analyzing cardiac activity signals sensed by the sensing circuit 244 and/or the DAS 250. The arrhythmia detector 234 is configured to analyze cardiac signals sensed at various sensing sites.

The microcontroller 220 further includes an AVD adjustment module 235 that is configured to perform, among other things, the operations of the methods described herein. The AVD adjustment module 235 is configured to implement program instructions to: detect an atrial paced (Ap) event or atrial sensed (As) event; measure an AV interval corresponding to an interval between the Ap event or the As event and a sensed ventricular (Vs) event, the AV interval associated with a current heart rate (HR); automatically dynamically adjust a first AV delay based directly on the measured AV interval; identify a scale factor between a base As-Vs interval and a base Ap-Vs interval associated with the current HR; calculate a second AV delay by scaling the first AV delay based on the scale factor; and manage a pacing therapy, utilized by the IMD, based on the first and second AV delays. The AVD adjustment module 235 determined the base As-Vs and base Ap-Vs intervals during a calibration mode. After calibration, the AVD adjustment module 235 enters a search mode to detect changes in the AV intervals.

When the AVD adjustment module 235 measures an AV interval that originates from a sensed atrial event, the AVD adjustment module 235 designates the first AV delay to represent a sensed AV delay (AVDs) and directly calculates the AVDs by subtracting an offset from the measured As-Vs interval. The offset may be a preprogrammed value entered by a physician and/or automatically identified by the IMD. Optionally, the offset may represent a percentage based offset that is calculated in accordance with one or more embodiments described in the related co-pending applications identified herein and incorporated by reference herein. The AVD adjustment module 235 indirectly sets the second AV delay, representing a paced AV delay (AVDp). The AVD adjustment module 235 calculates the scaled AVDp by multiplying or dividing the AVDs by the scale factor determined from the base intervals.

Alternatively, during the search mode, when the AV interval that is measured originates from a paced atrial event, the AVD adjustment module 235 designates the first AV delay to represent a paced AV delay (AVDp). The AVDp is calculated by subtracting an offset from the measured Ap-Vs interval. The AVD adjustment module 235 defines the second AV delay to represent a sensed AV delay (AVDs). The scaled AVDs is calculated by multiplying or dividing the AVDp by the scale factor.

During a calibration mode derives one or more scale factor in connection with one or more HR ranges. For each HR range, the AVD adjustment module 235 may be further configured to measure the base As-Vs interval and the base Ap-Vs interval during heart beats that are in a common base HR range. The AVD adjustment module 235 stores a scale factor in connection with each base HR range. Thereafter, during operation to dynamically adjust the AV delay (e.g., FIG. 3B), the AVD adjustment module 235 identifies one of the scale factors to be used based on the current HR identified during a search mode. The AVD adjustment module 235 may be further configured to repeat the measure and store operations in connection with different base HR ranges to obtain a plurality of the base As-Vs intervals and the base Ap-Vs intervals associated with the different base HR ranges. When multiple scale factors are determined for different HR ranges, during the operations of FIG. 3B, the AVD adjustment module 235 identifies a select base HR range, from the multiple base HR ranges, that corresponds to the current HR and utilizes the scale factor associated with the select base HR range to calculate the second AV delay.

Additionally or alternatively, during a search window, the AVD adjustment module 235 may be further configured to extend the first and second AV delays to correspond to a default search AV delay ($AVD_{search}$). The AVD adjustment module 235 senses cardiac activity for a predetermined number of cardiac beats during the search window, identifies whether the cardiac activity is indicative of a conduction block condition or non-conduction block condition, and repeats the determine, calculate and adjust operations only when the non-conduction block condition is identified.

Additionally or alternatively, the AVD adjustment module 235 identifies the cardiac activity to be indicative of a conduction block condition when fewer than a select number of cardiac beats exhibit sensed ventricular events during the default search AV delay $AVD_{search}$.

Additionally or alternatively, the AVD adjustment module 235 may designate the first and second AV delays to correspond to a sensed AV delay (AVDs) and a paced AV delay (AVDp). The AVD adjustment module 235 may be further configured to identify a presence of conduction block and, in response thereto, revert the AVDs and AVDp to base AVDs-base and base AVDp-base programmed lengths, respectively; and maintain the base AVDp-base and base AVDs-base programmed lengths for a select second number of cardiac beats.

Additionally or alternatively, the AVD adjustment module 235 may be configured to perform the operations discussed above and described hereafter in connection with sensing intrinsic activity at a HIS bundle site (HISs) and delivering pacing pulses at the HIS bundle site. For example, the HIS bundle sensing/pacing site may be substituted for one or more right ventricular sensing/pacing sites. As another example, the HIS bundle sensing/pacing site may be substituted for one or more left ventricular sensing/pacing sites. When the HIS bundle sensing/pacing site is substituted for a left or right ventricular sensing/pacing site, the operations described herein are preformed between sensed or paced atrial events and sensed HIS bundle events, instead of sensed ventricular events.

The microcontroller 220 is operably coupled to a memory 260 by a suitable data/address bus 262. The programmable operating parameters used by the microcontroller 220 are stored in the memory 260 and used to customize the operation of the IMD 100 to suit the needs of a particular patient. The operating parameters of the IMD 100 may be non-invasively programmed into the memory 260 through a telemetry circuit 264 in telemetric communication via communication link 266 (e.g., MICS, Bluetooth low energy, and/or the like) with the external device 254.

The IMD 100 can further include one or more physiological sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis. While shown as being included within the IMD 100, the physiological sensor(s) 270 may be external to the IMD 100, yet still, be implanted within or carried by the patient. Examples of physiological sensors might include sensors that, for example, sense respiration rate, pH of blood, ventricular gradient, activity, position/posture, minute ventilation (MV), and/or the like.

A battery 272 provides operating power to all of the components in the IMD 100. The battery 272 is capable of operating at low current drains for long periods of time, and is capable of providing a high-current pulses (for capacitor charging) when the patient requires a shock pulse (e.g., in excess of 2 Å, at voltages above 2 V, for periods of 10 seconds or more). The battery 272 also desirably has a predictable discharge characteristic so that elective replacement time can be detected. As one example, the IMD 100 employs lithium/silver vanadium oxide batteries.

The IMD 100 further includes an impedance measuring circuit 274, which can be used for many things, including sensing respiration phase. The impedance measuring circuit 274 is coupled to the switch 226 so that any desired electrode and/or terminal may be used to measure impedance in connection with monitoring respiration phase.

The microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 11 to 40 joules), as controlled by the microcontroller 220. Such shocking pulses are applied to the patient's heart through shocking electrodes. Maybe noted that the shock therapy circuitry is optional and may not be implemented in the IMD 100.

The microcontroller 220 further includes timing control 232 used to control the timing of such stimulation pulses (e.g., pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. The switch 226 includes a plurality of switches for connecting the desired electrodes to the appropriate I/O circuits, thereby providing complete electrode programmability. Accordingly, the switch 226, in response to a control signal 228 from the microcontroller 220, determines the polarity of the stimulation pulses (e.g., unipolar, bipolar, etc.) by selectively closing the appropriate combination of switches (not shown) as is known in the art.

The microcontroller 220 is illustrated to include timing control 232 to control the timing of the stimulation pulses (e.g., pacing rate, atrioventricular (AV) delay, atrial interconduction (A-A) delay, or ventricular interconduction (V-V) delay, etc.). The AV delay is managed to provide a fusion AV delay to fuse timing of pacing pulses with intrinsic wave fronts. The timing control 232 may also be used for the timing of refractory periods, blanking intervals, noise detection windows, evoked response windows, alert intervals, marker channel timing, and so on. Microcontroller 220 also has a morphology detector 236 to review and analyze one or more features of the morphology of cardiac signals. Although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication with other devices, implanted devices and/or external devices. In one implementation, the communication modem 240 may use high-frequency modulation of a signal transmitted between a pair of electrodes. As one example, the signals may be transmitted in a high-frequency range of approximately 10-80 kHz, as such signals travel through the body tissue and fluids without stimulating the heart or being felt by the patient.

Figure 3A:
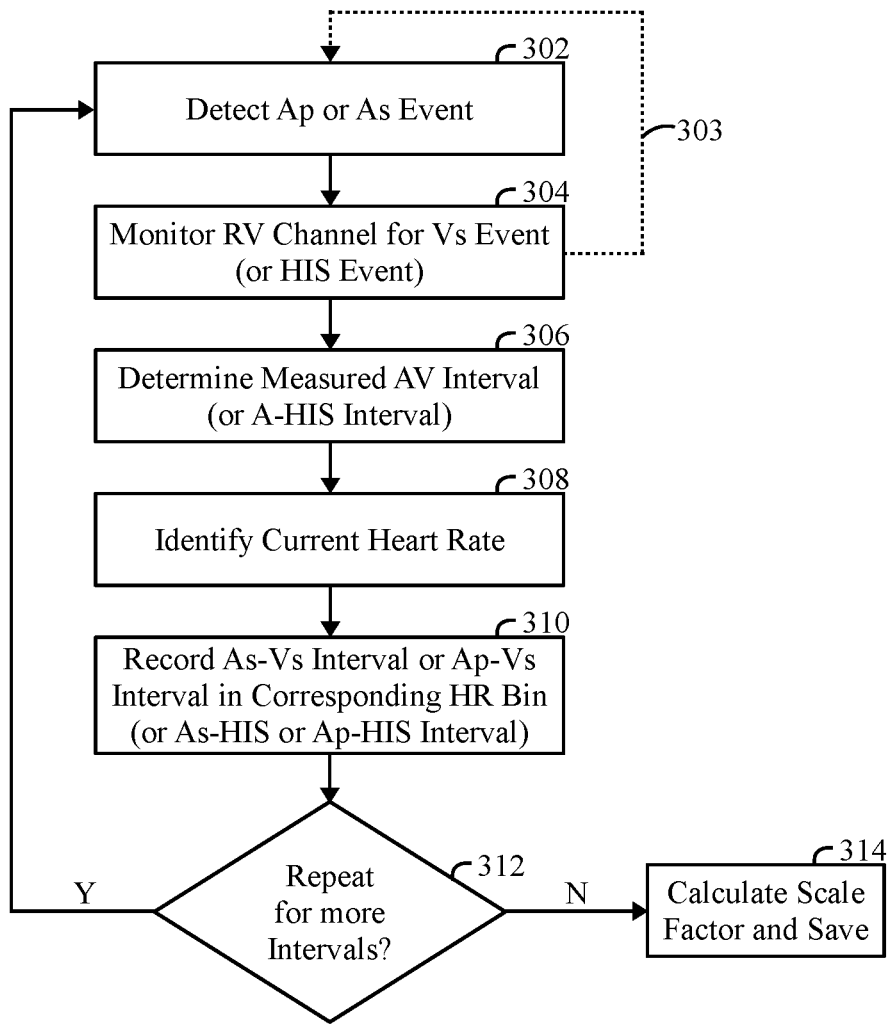
FIG. 3A illustrates a computer implemented method for measuring and binning AV intervals and calculating scale factors in accordance with embodiments herein.

FIG. 3A illustrates a computer implemented method for measuring and binning AV (and/or A-HIS) intervals and calculating scale factors in accordance with embodiments herein. The method is under control of one or more processors configured with specific executable instructions. The method may be implemented in part, or entirely, by one or more processors of an IMD. Additionally or alternatively, the method may be implemented in part, or entirely, by one or more processors of a local external device (e.g., a smart phone, bedside monitor, clinician programmer) and/or a remote server. As explained hereafter, the operations of FIG. 3A may be performed during a calibration and/or during a search mode in connection with an AV synchrony setting operation. Optionally, the operations of FIG. 3A may be performed following termination of the search mode after an identification of whether a patient is experiencing normal conduction or an abnormal conduction block condition. Optionally, the operations of FIG. 3A may be performed when the heart rate changes and moves from one HR range to another HR range. The operations of FIG. 3A are described primarily in connection with atrial and ventricular events, but it is understood that the operations may be performed in connection with atrial and HIS bundle events instead of or in addition to performing the operations in connection with atrial and ventricular events.

At 302, the one or more processors detect a paced atrial (Ap) event or sensed atrial (As) event. When the paced or sensed atrial event is detected, one or more AV interval timers are started.

At 304, the one or more processors monitor an RV sensing channel for a sensed ventricular (Vs) event. The Vs event may occur at an RV sensing site or an LV sensing site, or both. Optionally, a sensed RV (RVs) event may be detected separate from a sensed LV (LVs) event.

At 304, the one or more processors automatically reduce a currently programmed pacing rate, such as by setting the base pacing rate to 5-10 bpm lower than a pacing rate that would otherwise be set based on the current intrinsic heart rate. By reducing the programmed pacing rate, the process of FIG. 3A allows an intrinsic atrial event to occur. The base pacing rate is only lowered by a few beats per minute (bpm), and thus if an intrinsic atrial event does not occur, even during the extended pacing rate, the IMD will ultimately deliver a therapy. In addition, the one or more processors also set the sensed AV delay to a duration that is greater than a time interval that would be otherwise set based on the intrinsic sensed atrial and sensed ventricular events. By lengthening the sensed AV delay, the process of FIG. 3A allows an intrinsic ventricular event to occur. The sensed AV delay is only lengthened by a predetermined amount, and thus if an intrinsic ventricular event does not occur, even during the extended sensed AV delay, the IMD will ultimately deliver a ventricular therapy.

At 306, the one or more processors determine a measured AV interval. The measured AV interval may correspond to an interval between a sensed atrial event and a sensed ventricular event (As-Vs interval) or an interval between a paced atrial event and a sensed ventricular event (Ap-Vs interval). The processors record the measured AV interval as an As-Vs interval or Ap-Vs interval based on whether the atrial event at 302 was a sensed event or a paced event, respectively.

Optionally, in accordance with embodiments herein, measurements may be performed between right atrial events and right ventricular events, as well as between right atrial events and left ventricular events, in connection with multipoint pacing (MPP) through right and left ventricular leads. When left ventricular sensing and pacing is implemented in accordance with embodiments herein, the abbreviations and nomenclature herein may separately refer to the right ventricular (RV) events and left ventricular (LV) events. For example, embodiments that utilize MPP may measure an interval between a sensed atrial event and a sensed left ventricular event (As-LVs interval) and/or an interval between a paced atrial event and a sensed left ventricular event (Ap-LVs interval).

It is recognized that in certain instances, a sensed ventricular event may not occur. When a sensed ventricular event does not occur, flow returns along 303 and the processors wait for detection of a new paced or sensed atrial event, after which the timers are reset.

Optionally, the operations at 302-306 may be performed multiple times (e.g., three-five times) in connection with obtaining As-Vs intervals that are then averaged or otherwise mathematically combined to obtain a mean or other mathematical combination representative of the As-Vs interval. Similarly, the operations at 302-306 may be performed multiple times in connection with obtaining Ap-Vs intervals that are then averaged or otherwise mathematically combined to obtain a mean or other mathematical combination representative of the Ap-Vs interval. The Ap-Vs interval is automatically measured by increasing the base pacing rate by a predetermined amount (e.g., 5-10 bpm) greater than a pacing rate otherwise indicated by the intrinsic heart rate. By increasing the base pacing rate, the process forces delivery of paced atrial events. In addition, the one or more processors also set the sensed AV delay to a duration that is greater than a time interval that would be otherwise set based on the intrinsic sensed atrial and sensed ventricular events. By lengthening the sensed AV delay, the process of FIG. 3a allows an intrinsic ventricular event to occur.

At 308, the one or more processors identify a current heart rate in connection with the As-Vs interval or Ap-Vs interval. For example, the heart rate may be defined in terms of the interval between the atrial and ventricular events. Additionally or alternatively, the interval between the atrial and ventricular events may be used to calculate a heart rate in beats per minute. Additionally or alternatively, the processors may track the heart rate in beats per minute separate from the intervals measured at 306.

The measured AES-Vs interval and Ap-Vs interval are heart rate dependent as, during normal AV conduction, faster heart rates result in faster conduction velocities. Accordingly, the operations at 306 and 308 measure the AES-Vs interval and Ap-Vs interval during similar heart rates or within a predetermined heart rate range.

At 310, the one or more processors record the As-Vs interval or Ap-Vs interval, such as in a heart rate bin corresponding to the heart rate identified at 308. For example, a series of heart rate (HR) bins may be maintained for different heart rate ranges (e.g., 30-50 bpm, 50-65 bpm, 65-80 bpm, 80-95 bpm, etc.). The duration may be the same or differ from one another for different heart rate ranges. For example, the durations of the individual heart rate ranges may vary based on a determination of which conduction times for As-Vs intervals and Ap-Vs intervals at different heart rates correlate more accurately to one another. As a further example, it may be determined that As-Vs intervals and Ap-Vs intervals in the HR range of 60-70 bpm should be binned together, but separate from As-Vs intervals and Ap-Vs intervals at heart rates below 60 bpm or above 70 bpm. As another example, the As-Vs intervals and Ap-Vs intervals in the HR range 70-95 may be binned together without an notable change on the scaling operations described herein.

At 312, the one or more processors determine whether to repeat the process for additional heart beats. If so, flow returns to 302. Otherwise, the process ends. The process of FIG. 3A repeats until the processors determine that a sufficient number of AV intervals have been measured in connection with paced atrial events and sensed atrial events and in connection with HR ranges of interest. For example, it may be desirable to obtain AV intervals for 5 or 10 As and Ap events. Additionally or alternatively, the decision at 312 may be based in part on whether a sufficient number of AV intervals are measured for each HR bin. For example, it may be desirable to measure 2-5 As-Vs intervals and 2-5 Ap-Vs intervals while the heart rate is in each of a select number of heart rate ranges (e.g., below 60 bpm, 60-90 bpm, 90-120 bpm, above 120 bpm). Once the desired number of AV intervals are measured for each type of atrial event and for each HR range of interest, flow moves to 314.

At 314, the one or more processors calculate a scale factor between a base AES-Vs interval and a base Ap-Vs interval associated with the current heart rate. The base AES-Vs interval and base Ap-Vs interval may be obtained during a single iteration through the operations at 302-310. Alternatively, the base AES-Vs interval and base Ap-Vs interval may be obtained based on averages or other mathematical combinations of measurements obtained during multiple iterations through the operations at 302-310. The processors store the scale factor in connection with the base HR range and, as explained herein the stored scale factor is utilized during subsequent adjustments of the AV delay when a subsequent (current) HR is within the base HR range.

To validate the processes herein, cardiac activity data was analyzed from a QRS evaluation study of 100 patients who had cardiac resynchronization therapy (CRT) devices implanted. The QRS evaluation study included approximately 30 minutes of cardiac activity data collected from each patient. During the 30 minute period for each patient, the patient's heart rate varied between different HR ranges. Over the 30 minute period of data collection, 49 of the patients exhibited Ap-Vs events and As-Vs events at heart rates that were within a common heart rate bin. For example, the 49 patients each exhibited at least one Ap-Vs event and at least one As-Vs event in a common heart rate bin (e.g., 60-70 bpm, 70-80 bpm, etc.). The Ap-Vs intervals and As-Vs intervals measured at heart rates within the common HR bin were analyzed to calculate the (average) base Ap-Vs interval and the (average) base As-Vs interval, respectively. For each heart rate range, a scale factor was then calculated from the ratio of the base As-Vs interval and base Ap-Vs interval (e.g., R=(mean Ap-Vs)/(mean As-Vs)). The scale factors were calculated for each heart rate bin, for which cardiac activity data was collected. For the 49 patients in the QRS evaluation study, the overall mean scale factor (R) was 1.27+/−0.31, with a range of 0.29 to 1.89. When outliers were removed and the scale factors within the 5-95 percentile range were retained, the mean ratio of the remaining 44 patients was R=1.31+/−0.21, with a range of 0.68 to 1.83. From the foregoing data, it seems clear that consistent scale factors, with little variation, can be derived for individual patients in connection with As-Vs and Ap-Vs intervals that are recorded in connection with heart rates within common heart rate bins.

The process of FIG. 3A for obtaining a scale factor may be performed a single time during one calibration operation for each patient. Alternatively, more complex implementations may involve frequent calibrations, wherein the operations of FIG. 3A are repeated based on various criteria. As explained herein, the scale factor or scale factors are used to calculate a second AV delay by scaling a first AV delay that is based directly on a measured AV interval.

In accordance with the operations of FIG. 3A, the base As-Vs interval and the base Ap-Vs interval are measured during different heart beats that occur while the heart rate is within a common base HR range. The processors repeat the measuring and storing operations in connection with different base HR ranges to obtain a plurality of the base As-Vs intervals and the base Ap-Vs intervals associated with the different base HR ranges. Thereafter, the processors identify a select base HR range from the plurality of base HR ranges that corresponds to the current HR. The processors utilize the scale factor associated with the select base HR range to calculate a second AV delay.

The operations of FIG. 3A may be performed during an in clinic visit, such as utilizing an external programmer device. Additionally or alternatively, the operations of FIG. 3A may be performed by the IMD during an in clinic visit or at home.

Optionally, the operations of FIG. 3A may be performed between an atrial site and a HIS bundle site. For example, the operation at 304 may monitor a HIS bundle channel for a sensed HIS bundle event. The operation at 306 may determine a measured atrial to HIS bundle interval, while the operation at 310 records the As-HISs Interval or Ap-HISs interval in a corresponding heart rate bin. The operation at 314 may calculate and save a corresponding scale factor between a base As-HISs interval and a base Ap-HISs interval associated with the current heart rate.

Optionally, the operations of FIG. 3A may be performed between an atrial site, one or more ventricular sites and a HIS bundle site.

Figure 3B:
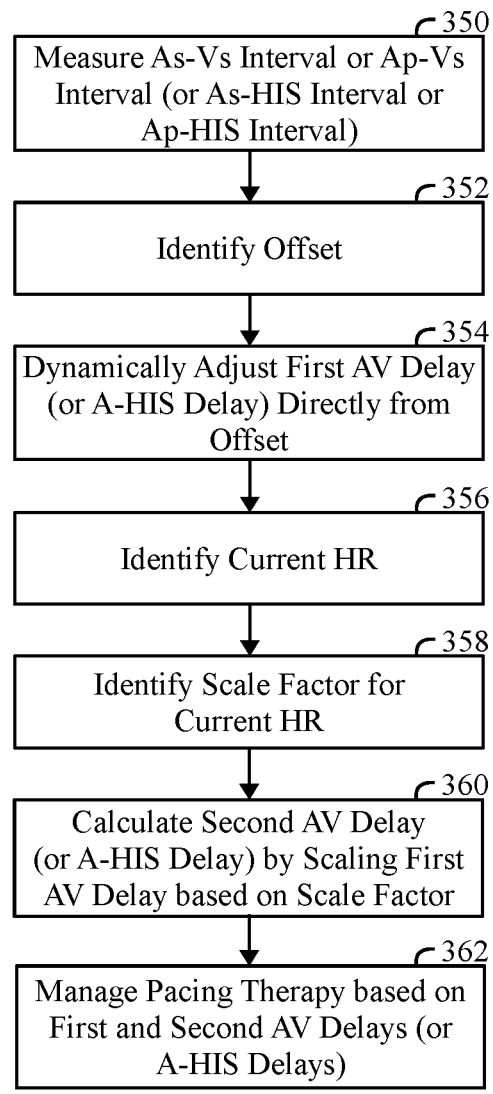
FIG. 3B illustrates a computer implemented method for setting AVDs and AVDp values, either directly or through scaling, in accordance with embodiments herein.

FIG. 3B illustrates a computer implemented method for setting AVDs and AVDp values, either directly or through scaling, in accordance with embodiments herein. The method is under control of one or more processors configured with specific executable instructions. The method may be implemented in part, or entirely, by one or more processors of an IMD. Additionally or alternatively, the method may be implemented in part, or entirely, by one or more processors of a local external device (e.g., a smart phone, bedside monitor, clinician programmer) and/or a remote server. As explained hereafter, the operations of FIG. 3B may be performed, by an IMD, during a search mode in connection with an AV synchrony setting operation. Optionally, the operations of FIG. 3B may be performed following termination of the search mode after an identification of whether a patient is experiencing normal conduction or an abnormal conduction block condition. Optionally, the operations of FIG. 3B may be performed when the heart rate changes and moves from one HR range to another HR range. The operations of FIG. 3B are described primarily in connection with atrial and ventricular events, but it is understood that the operations may be performed in connection with atrial and HIS bundle events instead of or in addition to performing the operations in connection with atrial and ventricular events.

At 350, the one or more processors measure an As-Vs interval or an Ap-Vs interval. For example, the processors may perform operations similar to the operations at 302-306 to detect an As or Ap event, start a timer and measure a time from the As or Ap event to a Vs event.

At 352, the one or more processors identify one or more offsets to be used to set the AVDs and AVDp. The offset may be programmed by a clinician and/or automatically derived by the IMD based on recorded physiologic characteristics. Optionally, the offset may be set to equal a percentage (e.g., 20%) of the measured AV interval, such as percentage based (PB) offset=(AV interval)*P1%, where P1% corresponds to a percentage that is programmed by a clinician and/or automatically derived by the IMD based on recorded physiologic characteristics. The offset may be determined based on the processes described in the above related co-pending application.

At 354, the one or more processors automatically dynamically adjust a first AV delay based directly on the measured AV interval. For example, when the AV interval measured represents a measured As-Vs interval, the first AV delay represents a sensed AV delay (AVDs) that is calculated by subtracting an offset from the measured As-Vs interval. Alternatively, when the AV interval measured represents a measured Ap-Vs interval, the first AV delay represents a paced AV delay (AVDp) that is calculated by subtracting an offset from the measured Ap-Vs interval.

At 356, the one or more processors identify a current heart rate associated with the measured As-Vs interval or Ap-Vs interval.

At 358, the one or more processors identify a scale factor associated with the current heart rate. As explained herein, the scale factor identifies a relation between a base As-Vs interval and base Ap-Vs interval for a common heart rate or heart rate range/bin. For example, the processors use the current heart rate to identify a corresponding HR bin. The processors obtain the scale factor associated with the current HR bin that includes the current HR. As a further example, it may be assumed that the processes for FIG. 3A generated scale factors of 1.2, 1.3 and 1.4 in connection with HR bins of 40-60 bpm, 60-70 bpm and 70-90 bpm, respectively. When the current HR is between 60 and 70 bpm, the processors obtain the scale factor of 1.3.

At 360, the one or more processors calculate a second AV delay by scaling the first AV delay based on the scale factor. For example, when the second AV delay represents a paced AV delay (AVDp), the AVDp is calculated by multiplying or dividing the AVDs by the scale factor. Alternatively, when the second AV delay represents a sensed AV delay (AVDs), the AVDs is calculated by multiplying or dividing the AVDp by the scale factor.

The determination of whether to multiply or divide the AVDp by the scale factor is dependent in part on what constitutes the numerator and denominator of the scale factor. For example, when the scale factor R is defined by the As-Vs interval divided by the Ap-Vs interval, the AVDp is scaled by AVDs*R, or the AVDs is scaled by AVDp/R. When the scale factor R=(Ap-Vs interval)/(As-Vs interval), the AVDs is scaled by AVDp*R, or the AVDp is scaled by AVDs/R.

At 362, the one or more processors manage pacing therapy, utilized by the IMD, based on the first and second AV delays.

Using the scale factor to convert between AVDp and AVDs values, embodiments herein account for (factor in) the patient-specific difference in As-Vs and Ap-Vs intervals which depend on relative locations of the atrial lead, sinoatrial node and atrioventricular node, as well as the respective conduction velocities. Automatically calculating the scale factor from direct measurements of the As-Vs interval and Ap-Vs interval, rather than generalizing the differences in sensed and paced AV delays, ensures that conversion to/from a sensed AV delay and a paced AV delay are individualized to each patient. The scaling factor utilizes a ratio between the As-Vs interval and Ap-Vs interval, in part, to cancel out dependence on heart rate. To the extent that heart rate is a function of both intervals, by utilizing As-Vs and Ap-Vs intervals within a common heart rate bin, the impact of the heart rate is canceled out.

As described herein, the scaling factor may be obtained during a single calibration operation for each patient. Optionally, the measurements of the As-Vs and Ap-Vs intervals may be performed by the IMD periodically (e.g., daily) and/or based on other criteria (e.g., exhibiting certain physiologic behavior). By periodically performing the calibration, embodiments herein update the scaling factor and account for any potential heart rate dependency.

In the foregoing embodiments, a separate scaling factor is stored in connection with each heart rate range. Additionally or alternatively, scaling factors for all heart rates and/or a subset of heart rate ranges can be combined, such as through averaging or some other mathematical operation.

Hereafter, an example implementation is described for an AV synchronization process that utilizes scaling factors and paced/sensed AV delays as described herein. Additionally or alternatively, the scaling factors and paced/sensed AV delays calculated herein may be utilized in connection with other therapy management processes, such as in connection with any IMD feature that adjust an AV delay and needs to account for transitions between atrial pacing and atrial sensing.

Optionally, the operations of FIG. 3B may be performed between an atrial site and a HIS bundle site. For example, the operation at 350 may determine a measured atrial (paced or sensed) to HIS bundle interval, while the operation at 350 to identify an offset based thereon. The operation at 354 may dynamically adjust a first A-HIS delay directly from the offset. The operation at 358 may identify a HIS scale factor for the current heart rate, while the operation at 360 calculates a second A-HIS delay by scaling the first A-HIS delay based on the scale factor. Optionally, the operations of FIG. 3B may be performed between an atrial site, one or more ventricular sites and a HIS bundle site.

Figure 4:
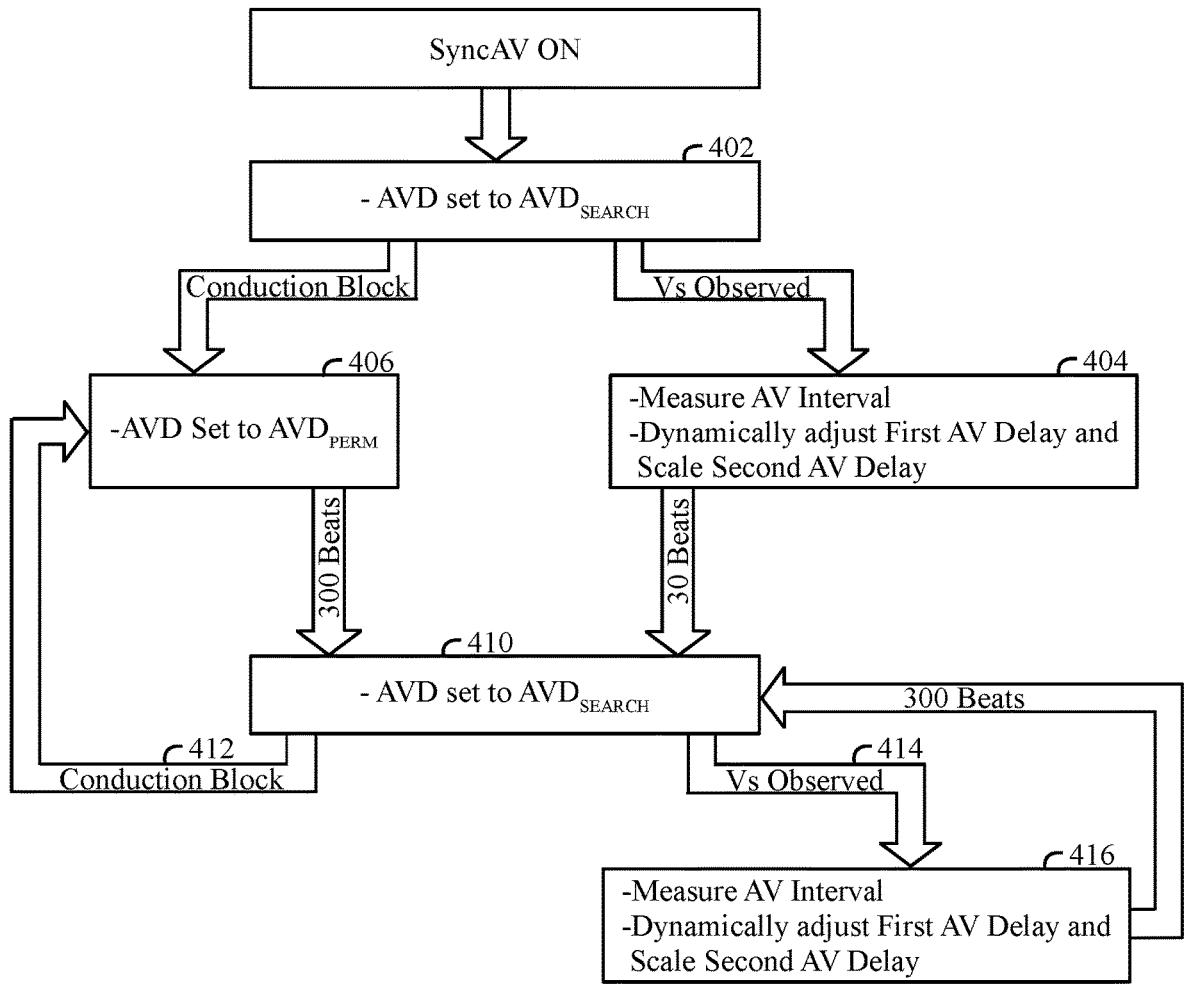
FIG. 4 illustrates an overall process for implementing AV synchronization in accordance with embodiments herein.

FIG. 4 illustrates an overall process for implementing AV synchronization in accordance with embodiments herein. The AV synchronization process utilizes the dynamic device-based AV delay adjustment process of FIGS. 3A and 3B.

At 402, when the AV synchronization process is activated, the one or more processors enter a search mode for a search window of predetermined duration. During the search mode, the processors set the AVDp and AVDs values to equal corresponding AV search delays (collectively referred to as AVDsearch). The AV search delays are set to be sufficiently long to wait for an intrinsic RV event that may be delayed following a paced atrial or sensed atrial event. However, the AV search delays, AVDsearch, are not too long in order to avoid delaying pacing when a patient should otherwise be paced. For example, the AVDsearch may be set to between 300 and 400 ms, and more preferably the AVDp may be set to equal 300 ms to 350 ms, while the AVDs may be set to equal 325 ms to 375 ms. Additionally or alternatively, a first AVDsearch may be set in connection with measuring an As-Vs interval (e.g., 325 ms), while a second AVDsearch may be set in connection with measuring an Ap-Vs interval (e.g., 350 ms). The processors may remain in the search mode for a search window corresponding to a predetermined number of beats (e.g., 5 beats, 10 beats) and/or a predetermined period of time (e.g., 10 second). Additionally or alternatively, the processors may remain in the search mode until a condition is satisfied, such as detecting a particular physiologic pattern (e.g., detecting 3 consecutive Vs events). While in the search mode, the processors track the cardiac activity.

When the search mode is terminated, the one or more processors determine whether the tracked cardiac activity is indicative of conduction block or whether a sufficient number of Vs events were detected. For example, when all or a select number of the beats, during the search mode, exhibit Vs events that are detected before the AVDsearch time expires, the processors may declare the series of beats to exhibit a normal or non-blocked condition, in response to which flow moves to 404. As a further example, during a series of 4-8 beats, 3 or more consecutive beats may exhibit sensed ventricular Vs events before the AVDsearch time expires, in which case the processors declare the series of events to be normal.

When flow advances to 404, the one or more processors measure one or more AV intervals and set the AVD based on the measured AV interval as described herein (e.g., in connection with the operations of FIGS. 3A and 3B). For example, as explained in connection with FIG. 3B, the measured AV interval represents an As-Vs interval when associated with an intrinsic atrial event. When an intrinsic atrial event occurs, the measured As-Vs interval is used to directly dynamically adjust the AVDs (representing a first AV delay). The AVDs is then multiplied by a scale factor (corresponding to the current heart rate) to calculate the second AV delay, corresponding to the AVDp, as a scaled version of the AVDs. Alternatively, when a paced atrial event occurs, at 404, the measured Ap-Vs interval is used to directly dynamically adjust the AVDp (representing the first AV delay). The AVDp is then multiplied by the scale factor to calculate the second AV delay, corresponding to the AVDs, as a scaled version of the AVDp.

The processors may use a select end or intermediate one of the beats measured during the search window, as the measured As-Vs or Ap-Vs interval. For example, following the start of the search mode (and setting the AV delays to the AVDsearch time, the processors may use the third or fourth event/beat as the measured As-Vs or Ap-Vs interval in order to allow for the AV interval to stabilize following the change to the AVDsearch time.

Optionally, when both types of atrial events occur during the search window (e.g., one or more beats with intrinsic atrial events and one or more beats with paced atrial events), the processors may select one type of atrial event and utilize the measures AV intervals associated with the select type of atrial event while disregarding any measured AV intervals associated with the non-selected type of atrial events. For example, when at least one event of a select type (e.g., sensed atrial event) occurs during the search window, the processors may default to use the measured AV interval (at 404 and 416) for the select type. Alternatively, the processors may utilize a particular cardiac beat from the search window (e.g., the $3^{rd}$ cardiac beat). Alternatively, the processors may utilize the measured AV intervals for the type of atrial event that occurred more frequently during the search window. For example, the As-Vs interval may be measured when 2-3 beats have intrinsic atrial events while only 1-2 beats have paced atrial events.

Optionally, the As-Vs interval or Ap-Vs interval may be calculated as an average (or other mathematical combination) of multiple As-Vs intervals and Ap-Vs intervals, respectively, for a desired number of multiple beats. For example, an average As-Vs interval may be calculated from all or a select number of the measured As-Vs intervals when a majority of the cardiac beats during the search window include intrinsic atrial events. Similarly, an average Ap-Vs interval may be calculated from all or a select number of the measured Ap-Vs intervals when a majority of the cardiac beats during the search window include paced atrial events. Optionally, the AVDs and AVDp may be set at 404 in various manners, based upon the nature of the events that occur during the search mode. For example, both of the AVDs and AVDp values may be set, as noted above in connection with FIG. 3B, in response to a select number (e.g., 3-5) consecutive Vs events occurring during the search mode (at 402).

Additionally or alternatively, the AVDs and AVDp delays may be set in alternative manners in response to other combinations of atrial and ventricular events occurring during the search mode. It may be desirable to utilize select combinations of atrial and ventricular events as a criteria for setting the AVDs and AVDp delays, such as in order to skip single or paired ectopic premature ventricular contractions (PVCs). For example, the one or more processors may search for a particular type of atrial event during a select beat within the search window. For example, the one or more processors may determine the type of atrial event that occurs during the third, fourth or fifth beat during the search mode, and based thereon, set the AVDs and AVDp delays in a desired manner. As a more specific example, when the processors determine that a sensed atrial As event occurs during the third beat, but before the third sensed ventricular event, the processors may set the AV delays as follows: AVDs=(As-Vs interval)−(offset) and AVDp=AVDs*R, where R is the scale factor between the measured base Ap-Vs interval and measured base As-Vs interval (e.g., R=(mean base Ap-Vs interval)/(mean base As-Vs interval)). In the foregoing example, the AVDs is set based directly on the As-Vs interval, while the AVDp is based on the AVDs and a scale factor and PBs offset. Alternatively, when the processors determine that a paced atrial Ap event occurs before the third sensed ventricular event, the processors may set the AV delays as follows: AVDp=(Ap-Vs interval)−(offset) and AVDs=AVDp/R. By setting the AVDs and AVDp based on the type of atrial event that occurred during the third or a later beat, the processors skip single or paired ectopic PVC beats.

The AVDp and AVDs values set at 404 are maintained for a select first number of cardiac beats (e.g., 20-40 beats) associated with a normal or non-conduction block condition.

Returning to 402, when fewer than the select number of the beats exhibit Vs events during the search window, the processors may declare the series of beats to exhibit an abnormal or conduction block condition. When an abnormal or conduction block condition is identified, flow moves to 406. For example, during the search mode, three consecutive Vs events may not occur. Alternatively, during the series of 4-8 beats, fewer than 3 consecutive beats may exhibit Vs events before the AVDsearch time expires.

At 406, the processors identify the presence of conduction block (or a similar abnormal condition), and in response thereto, revert the AVDs and AVDp delays to base programmed lengths (e.g., set AVDp-base equal to 100 ms to 150 ms and set AVDs-base equal to 125 ms to 175 ms). The base AVDp-base and AVDs-base lengths are maintained for a select extended second number of cardiac beats (e.g., 200-300 beats).

The AVDp and AVDs values set at 404 or 406 are utilized by the IMD for corresponding numbers of cardiac beats (e.g., 20-40 or 200-300), and thereafter flow continues to 410. At 410, after the corresponding number of select cardiac beats, the one or more processors reset the AVDp and AVDs values to the AV search delay AVDsearch, thereby reentering a search mode. The AV search delays set at 410 may be the same as or differ from the AV search delays set at 402. The duration of the search mode at 410 may be the same as or different from the duration of the search mode at 402. For example, the processors may maintain the search mode at 410 for 5 or more beats with the AVDp=350 ms and AVDs=325 ms. At 410, the one or more processors determine whether a select number of consecutive sensed ventricular Vs events occur and based thereon, flow branches along 412 or 414. For example, when three or another number of consecutive Vs events are detected during the search window, flow branches along 414.

At 414, the one or more processors measure one or more AV intervals and set the AVDp and AVDs based on the measured AV intervals and PB offsets. As explained above in connection with 404, at 416, one of the As-Vs interval and Ap-Vs interval are measured and used to directly adjust the corresponding one of the AVDs and AVDp values. The other one of the AVD S and a VDP are then indirectly calculated as a scaled version of the former. More specifically, when the measured AV interval represents an As-Vs interval, the measured As-Vs interval is used to directly dynamically adjust the AVDs (representing the first AV delay). The AVDs is then multiplied by a scale factor to calculate the second AV delay, corresponding to the AVDp, as a scaled version of the AVDs. Alternatively, when a paced atrial event occurs, at 410, the measured Ap-Vs interval is used to directly dynamically adjust the AVDp (representing the first AV delay). The AVDp is then multiplied by a scale factor to calculate the second AV delay, corresponding to the AVDs, as a scaled version of the AVDp. Thereafter, the AVDp and AVDs values set at 416 are maintained for a select number of cardiac beats (e.g., 200-300 beats).

Returning to 410, when the one or more processors determine that fewer than the select number of consecutive sensed ventricular Vs events occur, the processors determined that the patient exhibited a conduction block condition and in response thereto, flow branches along 412 and returns to 406. For example, the processors may identify a conduction block condition when the processors do not detect three or another select number of consecutive sensed ventricular Vs events during the search mode, and flow branches along 412. As noted above, at 406, the AVDp and AVDs values revert to the base programmed lengths for a longer select number of beats, such as 300×2N beats before reentering the search mode again. The variable N equals the number of consecutive searches in which conduction block was identified.

Additionally or alternatively, anytime the select number of consecutive sensed ventricular Vs events occur while the AVDp and AVDs values are already reduced (e.g., within either a 30 or 300 beat window), both AVDp and AVDs values are further reduced, as described above, such as for another 30 beats before re-entering the search mode. Additionally or alternatively, whenever the processors determine that it is desirable to further reduce the AVDp and AVDs values, after already being reduced, the processors may first enter the search mode for a shortened search window (e.g., after 30 beats instead of 300 beats) to allow the processors to perform a fast AV interval assessment.

The foregoing process of FIG. 3B for dynamically adjusting paced and sensed AV delays is described in connection with one example of an overall synchronization process (FIG. 4). Optionally, the dynamic process of FIG. 3B may be implemented in connection with other static or dynamic methods for programming paced and sensed AV delays.

The foregoing operations are described in connection with pacing and sensing events in the right atrium and right ventricle. Additionally or alternatively, embodiments herein may be implemented in connection with paced and sensed events in the left ventricle. For example, the one or more processors monitor for and detect a right sensed ventricular RVs event, and monitor for and detect a left sensed ventricular LVs event. The RVs event occurs at an RV sensing site and the LVs event occurs at an LV sensing site. When the LV lead includes multiple electrodes, such as in connection with multipoint pacing (MPP), various ones of the LV electrodes may be designated to be utilized as the LV sensing site. By way of example, the distal or one of the intermediate LV sensing sites may be utilized to monitor for and detect left sensed ventricular events.

The operations of FIG. 3B may be repeated or supplemented where the measure A-LV interval may correspond to an interval between a sensed atrial event and a sensed left ventricular event (As-LVs interval) and/or an interval between a paced atrial event and a sensed left ventricular event (Ap-LVs interval). The one or more processors calculate a scaling factor (R) as a ratio of the measured base As-LVs interval(s) and base Ap-LVs interval(s) [R=(As-LVs interval)/(Ap-LVs interval)]. Additionally or alternatively, the scaling factor may be calculated as a percentage P1% of the ratio of the measured base As-LVs interval and base Ap-LVs interval [R=(As-LVs interval)/(Ap-LVs interval)*P1%], where the P1% corresponds to a percentage that is programmed by a clinician and/or automatically derived by the IMD based on recorded physiologic characteristics.

When implement it in connection with multipoint pacing, the operations of FIG. 3B may be repeated in connection with left ventricular pacing and sensing sites. For example, the one or more processors automatically and dynamically directly adjust at least a first A-LV delay and indirectly calculate a second A-LV delay by scaling the first A-LV delay. For example, at 350, when the one or more processors measure an As-LVs interval, the processors directly set a sensed atrial event to sensed left ventricular event as A-LVDs=[(As-LVs interval)−(offset)]. The processors indirectly set a delay associated with a paced atrial event to sensed left ventricular event based on the scaling factor as A-LVDp=A-LVDs*R. Similarly, when the one or more processors measure an Ap-LVs interval, the processors directly set a paced atrial event to sensed left ventricular event as A-LVDp=[(Ap-LVs interval)−(offset)]. The processors indirectly set a delay associated with a sensed atrial event to sensed left ventricular event based on the scaling factor as A-LVDs=A-LVDp*R.

Optionally, the proposed independent A-RV and A-LV delays, may be expanded for use with multiple LV pacing/sensing sites. With biventricular MPP, AVDs and AVDp values for three or more pacing sites (RV, LV1, LV2, etc.) may be dynamically programmed: A-RVDs and A-RVDp, A-LVDs1 and A-LVDp1, and A-LVDs2 and A-LVDp2. Optionally, with LV-only MPP, only two AVD values would be dynamically programmed: A-LVDs1 and A-LVDp1, and A-LVDs2 and A-LVDp2 such as for an intermediate and distal electrodes.

CLOSING

The various methods as illustrated in the Figures and described herein represent exemplary embodiments of methods. The methods may be implemented in software, hardware, or a combination thereof. In various of the methods, the order of the steps may be changed, and various elements may be added, reordered, combined, omitted, modified, etc. Various of the steps may be performed automatically (e.g., without being directly prompted by user input) and/or programmatically (e.g., according to program instructions).

Various modifications and changes may be made as would be obvious to a person skilled in the art having the benefit of this disclosure. It is intended to embrace all such modifications and changes and, accordingly, the above description is to be regarded in an illustrative rather than a restrictive sense.

Various embodiments of the present disclosure utilize at least one network that would be familiar to those skilled in the art for supporting communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

All references, including publications, patent applications and patents, cited herein are hereby incorporated by reference to the same extent as if each reference were individually and specifically indicated to be incorporated by reference and were set forth in its entirety herein.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and physical characteristics described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. A method for dynamic device based AV delay adjustment, the method comprising:
providing electrodes configured to be located proximate to an atrial (A) site and a right ventricular (RV) site;
utilizing one or more processors for:
detecting an atrial paced (Ap) event or atrial sensed (As) event;
measuring an AV interval corresponding to an interval between the Ap event or the As event and a sensed ventricular (Vs) event;
automatically dynamically adjusting a first AV delay based directly on the measured AV interval to define a corresponding one of a paced or sensed AV delay (AVDp or AVDs);
identifying a scale factor, the scale factor representing a relation between a base As-Vs interval and a base Ap-Vs interval;
calculating a second AV delay by scaling the first AV delay based on the scale factor to define a corresponding other one the AVDp or AVDs; and
managing a pacing therapy, utilized by the IMD, based on the AVDp and AVDs.

2. The method of claim 1, wherein the AV interval measured represents a measured As-Vs interval and the first AV delay represents the sensed AV delay that is calculated by subtracting an offset from the measured As-Vs interval.

3. The method of claim 2, wherein the second AV delay represents the paced AV delay that is calculated by multiplying or dividing the AVDs by the scale factor, the scale factor representing a ratio between a base As-Vs interval and a base Ap-Vs interval.

4. The method of claim 1, wherein the AV interval measured represents a measured Ap-Vs interval and the first AV delay represents the paced AV delay AVDp that is calculated by subtracting an offset from the measured Ap-Vs interval.

5. The method of claim 4, wherein the second AV delay represents the sensed AV delay AVDs that is calculated by multiplying or dividing the AVDp by the scale factor.

6. The method of claim 1, further comprising measuring a base As-Vs interval and a base Ap-Vs interval; calculating the scale factor as a ratio between the base As-Vs interval and Ap-Vs interval; and storing the scale factor.

7. The method of claim 6, further comprising repeating the measuring, calculating and storing operations in connection with different base heart rate (HR) ranges to obtain a plurality of the base As-Vs intervals and the base Ap-Vs intervals associated with the different base HR ranges, wherein the identifying operation comprises identifying a select base HR range from the base HR ranges that corresponds to the current HR and utilizes the scale factor associated with the select base HR range to calculate the second AV delay.

8. The method of claim 1, further comprising, during a search window, extending the first and second AV delays to correspond to a default search AV delay ($AVD_{search}$); sensing cardiac activity for a predetermined number of cardiac beats during the search window; identifying whether the cardiac activity is indicative of a conduction block condition or non-conduction block condition; and repeating the determining, calculating and adjusting operations only when the non-conduction block condition is identified.

9. The method of claim 8, wherein the identifying operation comprises identifying the cardiac activity to be indicative of a conduction block condition when fewer than a select number of cardiac beats exhibit sensed ventricular events during the default search AV delay $AVD_{search}$.

10. The method of claim 1, wherein the scale factor is between a base As-Vs interval and a base Ap-Vs interval.

11. An implantable medical device (IMD), comprising:
electrodes configured to be located proximate to an atrial (A) site and a right ventricular (RV) site;
memory to store program instructions;
one or more processors configured to implement the program instructions to:
detect an atrial paced (Ap) event or atrial sensed (As) event;
measure an AV interval corresponding to an interval between the Ap event or the As event and a sensed ventricular (Vs) event;
automatically dynamically adjust a first AV delay based directly on the measured AV interval to define a corresponding one of a paced or sensed AV delay (AVDp or AVDs);
identify a scale factor, the scale factor representing a relation between a base As-Vs interval and a base Ap-Vs interval;
calculate a second AV delay by scaling the first AV delay based on the scale factor to define a corresponding other one the AVDp or AVDs; and
manage a pacing therapy, utilized by the IMD, based on the AVDp and AVDs.

12. The IMD of claim 11, wherein the AV interval measured represents a measured As-Vs interval and the first AV delay represents the sensed AV delay that is calculated by subtracting an offset from the measured As-Vs interval.

13. The IMD of claim 12, wherein the second AV delay represents the paced AV delay that is calculated by multiplying or dividing the AVDs by the scale factor.

14. The IMD of claim 11, wherein the AV interval measured represents a measured Ap-Vs interval and the first AV delay represents the paced AV delay AVDp that is calculated by subtracting an offset from the measured Ap-Vs interval.

15. The IMD of claim 14, wherein the second AV delay represents the sensed AV delay AVDs that is calculated by multiplying or dividing the AVDp by the scale factor.

16. The IMD of claim 11, wherein the one or more processors are further configured to measure the base As-Vs interval and the base Ap-Vs interval; and store the scale factor.

17. The IMD of claim 16, wherein the one or more processors are further configured to repeat the measure and store operations in connection with different base heart rate (HR) ranges to obtain a plurality of the base As-Vs intervals and the base Ap-Vs intervals associated with the different base HR ranges, wherein the identify operation comprises identifying a select base HR range from the base HR ranges that corresponds to the current HR and utilizes the scale factor associated with the select base HR range to calculate the second AV delay.

18. The IMD of claim 11, wherein the one or more processors are further configured to, during a search window, extend the first and second AV delays to correspond to a default search AV delay ($AVD_{search}$); sense cardiac activity for a predetermined number of cardiac beats during the search window; identify whether the cardiac activity is indicative of a conduction block condition or non-conduction block condition; and repeat the measure, adjust and calculate operations only when the non-conduction block condition is identified.

19. The IMD of claim 11, wherein the one or more processors are further configured to: measure an As-Vs interval corresponding to an interval between the Ap event and the Vs event; and measure an Ap-Vs interval between the As event and another Vs event.

\* \* \* \* \*